United States Patent
Michnick et al.

[19]

[11] Patent Number: 5,810,589
[45] Date of Patent: Sep. 22, 1998

[54] DENTAL IMPLANT ABUTMENT COMBINATION THAT REDUCES CRESTAL BONE STRESS

[75] Inventors: Bruce T. Michnick, Plainview; Gary Kitzis, Dix Hills; Ron Beauman, Hicksville, all of N.Y.

[73] Assignee: Dentistry Researchers & Designers Inc., Woodbury, N.Y.

[21] Appl. No.: 745,432

[22] Filed: Nov. 12, 1996

Related U.S. Application Data

[63] Continuation of Ser. No. 401,985, Mar. 10, 1995, abandoned.

[51] Int. Cl.[6] .................................................. A61C 8/00
[52] U.S. Cl. .......................... 433/169; 433/173; 433/174
[58] Field of Search .................................. 433/169, 172, 433/173, 174, 175

[56] References Cited

U.S. PATENT DOCUMENTS

| | | | |
|---|---|---|---|
| 4,177,562 | 12/1979 | Miller et al. | 433/174 |
| 5,030,095 | 7/1991 | Niznick | 433/174 |
| 5,169,309 | 12/1992 | Staubli et al. | 433/174 |
| 5,194,000 | 3/1993 | Dury | 433/173 |
| 5,372,503 | 12/1994 | Elia | 433/173 |
| 5,376,004 | 12/1994 | Mena | 433/174 |

*Primary Examiner*—Cary E. O'Connor
*Attorney, Agent, or Firm*—Charles I. Brodsky

[57] ABSTRACT

A dental implant-abutment combination that absorbs the forces of chewing, shifts some of the horizontal loads to a more vertical plane, shifts the horizontal loads which remain, to a point below the crest of the bone, lowers the pivoting axis, and distributes the forces over a larger surface area, all so as to prevent saucerization in the bone surrounding the implant, thereby preventing bacteria from gaining access to the deeper areas, and preventing implant failure due to the loss of supporting bone.

17 Claims, 5 Drawing Sheets

DENTAL IMPLANT ABUTMENT COMBINATION THAT REDUCES CRESTAL BONE STRESS

This application is a continuation of Application Ser. No. 08/401,985, filed Mar. 10, 1995, now abandoned.

FIELD OF THE INVENTION

This invention relates to the manner of attaching a replacement tooth or teeth in a mouth and, more particularly, to a new and improved dental implant - abutment combination.

BACKGROUND OF THE INVENTION

As is well known, people do not take care of their teeth as well as they should. This often results in the dental need to remove an entire tooth, or several teeth, due to excessive decay, fracturing, or periodontal disease. As is also known, where a stationary dental bridge is to be used, it needs to be secured to some solid structure due to the fact that there are significant forces at work during chewing. Frequently, there is insufficient numbers of teeth, or tooth structure remaining to secure a crown, so that the new bridge needs to be secured to the underlying bone by means of an implant and abutment combination.

Typically, such an implant consists of a cylindrical post having a uniform diameter over its entire length, and a threaded internal cavity which starts at the top end and extends centrally inward. The implant is inserted into a hole of uniform diameter in the bone in vertical orientation, with the implant's top edge being at a level flush with the crest of the bone. A healing screw is then inserted into the central cavity and the soft tissue closed over to allow healing and bone growth around the implant for a period of 3–8 months. After being thus integrated into the bone, the soft tissue is removed, exposing the healing screw which is then removed to permit the subsequent attachment of the abutment — to which a replacement tooth is attached. When the abutment is screwed into the implant, their two surfaces fit flush together so as to become a single unit, thereby securing the abutment in place.

One problem with this follows from the fact that when a person chews, significant forces which are built up need to be resisted by the bone in which the implant is embedded; this prior art arrangement simply does not permit adequate distribution of such forces, and the corresponding stresses. In particular, when this typical implant-abutment arrangement is loaded by chewing, the force is not in a 90-degree vertical plane, thereby placing a horizontal force component on the combination. Although the bone is loaded by an equal and opposite force, distributed along the entire surface of the implant, there concurrently is produced a bending moment in a direction to rotate the implant. The highest concentration of bending moment is opposed by the crest of the bone, with a minimal amount of the bending moment being opposed by the softer bone matrices around the bottom of the implant. Unlike force, the bending moment is not distributed along the entire surface of the implant, however. The result — with the crest of the bone being the point of highest stress concentration — has been noted to be a saucerization, the resorption of the bone around the top of the implant. Such saucerization results in the lengthening of the amount of implant exposed, thereby increasing stresses, and resorbing the bone faster. The end result may be that 1) if enough of the implant becomes exposed, the implant would fail and have to be removed; and 2) the bacterial build-up in the gap that develops accelerates the decay of bone, leads to infection, and possible loss of the implant.

OBJECTS OF THE INVENTION

It is an object of the present invention to provide a new method of securing replacement teeth to bone.

It is an additional object of the invention to accomplish this by a novel dental implant & abutment used in combination or separately.

It is also an object of the invention to prevent saucerization of the crestal bone area around the implant, to deter implant failure.

It is another object of the invention to prevent bacteria build-up around the implant, also to deter implant failure.

It is a further object of the invention to affix the implant to the bone in substantially the same manner as has traditionally been done, so as not to require the learning of near dental techniques.

SUMMARY OF THE INVENTION

As will become clear from the description that follows, the dental implant and abutment invention preferably is in the nature of an inexpensively priced, durable set designed to significantly reduce saucerization of the bone crest by relocating the point of maximum stress, and redistributing the stresses involved in chewing. As will become clear, the implant of the invention may be generally constructed in the form of a post, having a variable outer diameter along its length, — such as a barrel shape — and a threaded internal cavity which is tapered at it opening. As will further become clear, the abutment of the invention screws into the central cavity of the implant with opposing tapered surfaces meeting to prevent the underside of the abutment from contacting the upper surface of the implant. In a preferred embodiment of the invention, a shock absorbing material is placed between the surfaces of the abutment and implant so as to reduce the initial impact to the bone.

BRIEF DESCRIPTION OF THE DRAWINGS

These and other features of the invention will be more clearly understood from a consideration of the following description, taken in connection with the accompanying drawings, in which.

DETAILED DESCRIPTION OF THE DRAWINGS

Figure 1:
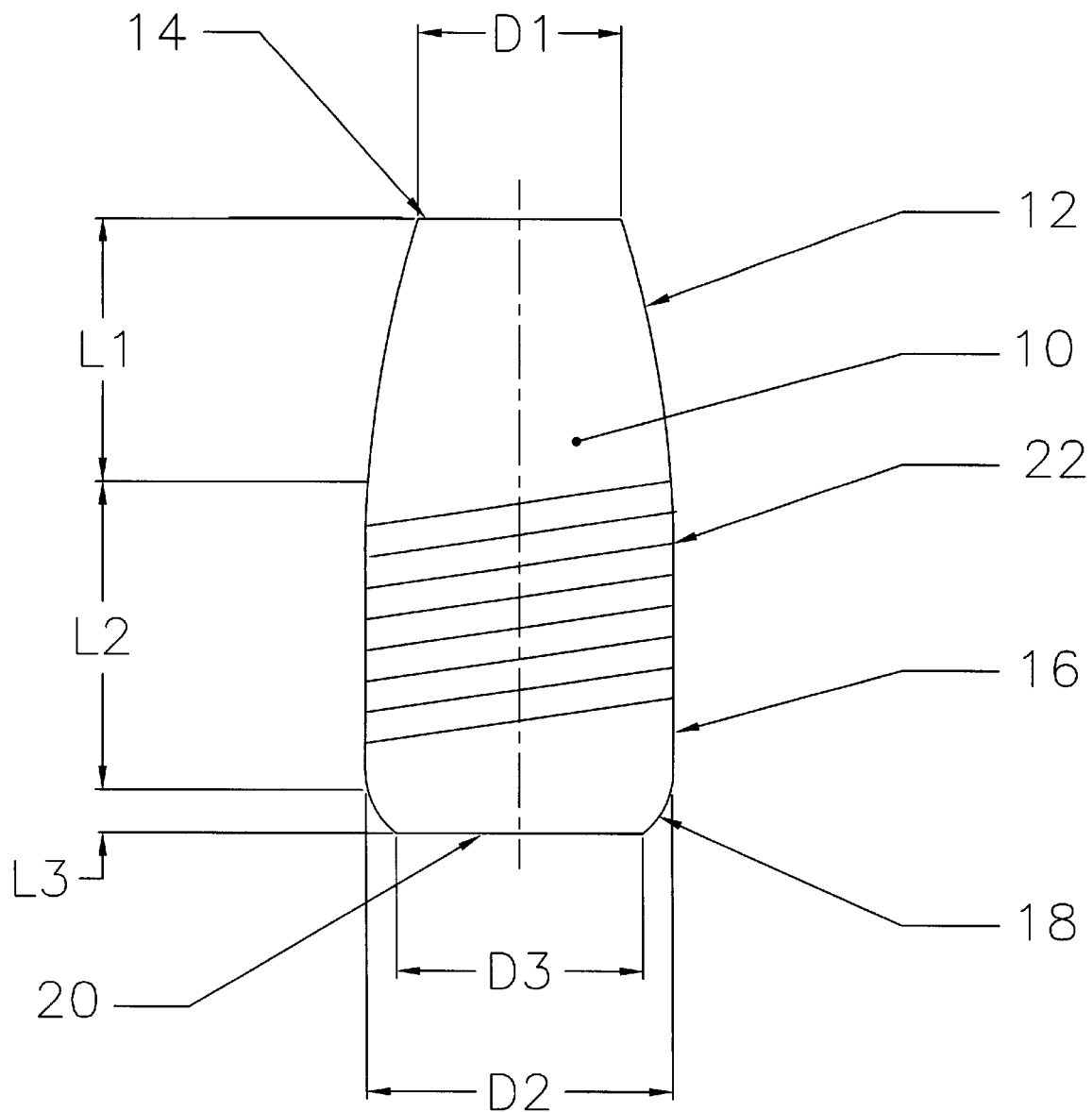
FIG. 1 is a side view of the dental implant of the invention.
Figure 2:
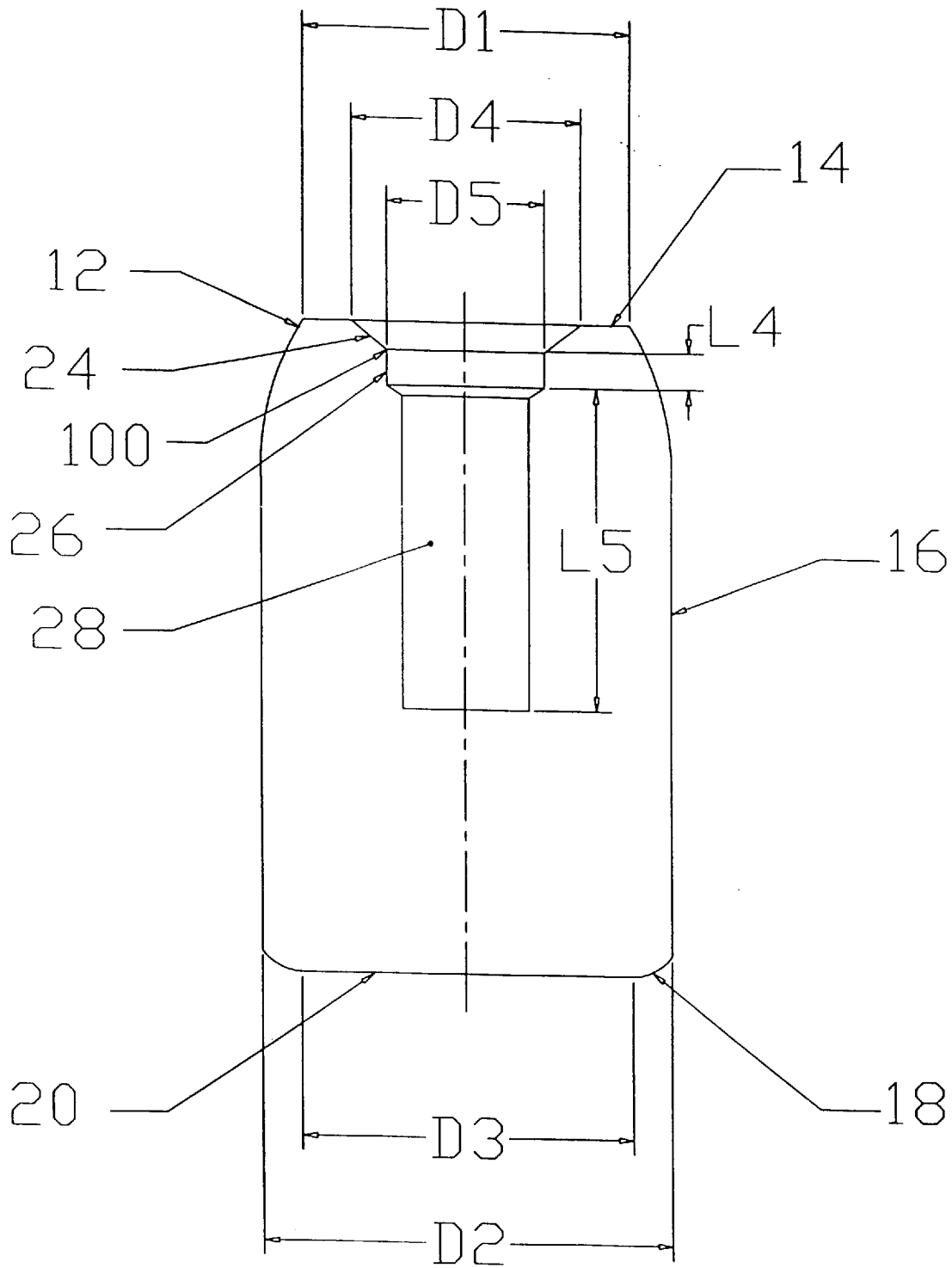
FIG. 2 is a side cut-away perspective view of the dental implant.
Figure 3:
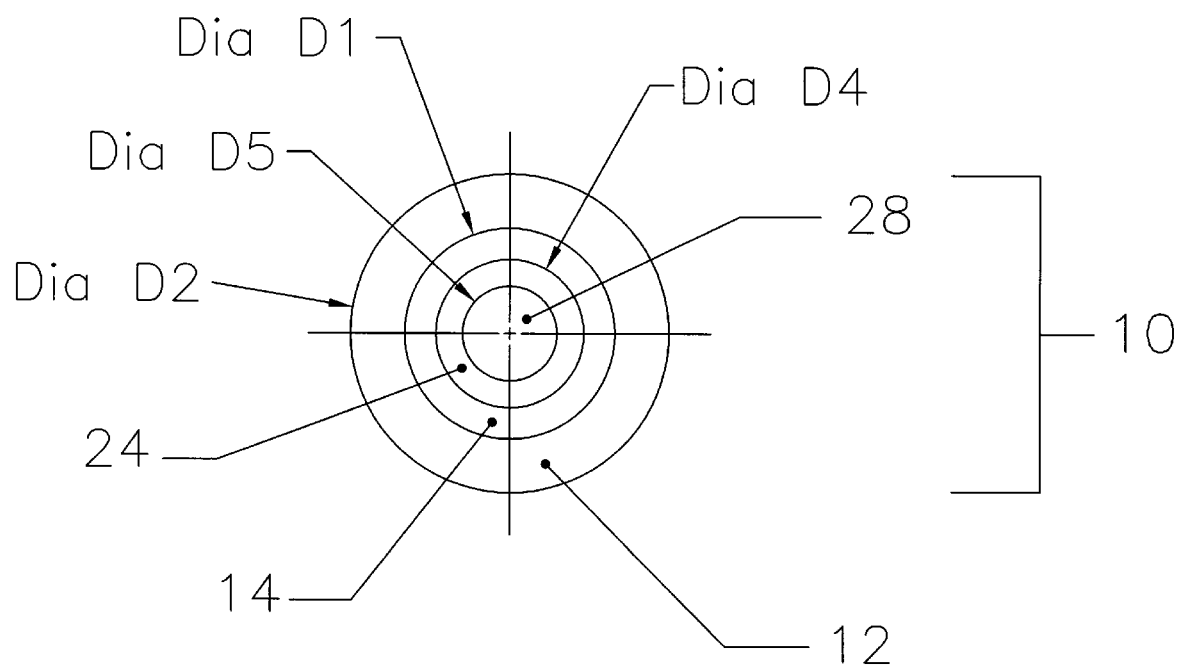
FIG. 3 is a top view of the dental implant according to the invention.

In FIGS. 1-3 the dental implant 10 is shown as having a curved body section 12, with an initial diameter $D_1$ and arcing outwardly and downwardly from the coronal lip 14 for a length $L_1$ with a radius — to become the body section 16 of a diameter $D_2$, and of a length $L_2$. A curved bottom segment 18 extends at the lower end of the body section 16, over a length $L_3$, with a radius to form the base of the implant 20, of a diameter $D_3$. In addition, — in a preferred embodiment of the invention — the body section 16, is provided with a threaded surface 22, for improved integration with bone.

FIG. 2 is a cut-away perspective view of the interior of the dental implant 10, showing a cavity opening — originating at the junction of surface 24 and the coronal lip 14 — having an initial diameter of $D_4$ and tapering centrally downward at an angle until it reaches a point 100, where it has a lesser diameter $D_5$. A thread guide 26, continues downward from the bottom of the surface 24 at a point 100 — maintaining the constant diameter $D_5$ — for a length $L_4$. A threaded central cavity 28, — threaded so as to accept the securing of a healing screw or dental abutment — extends centrally downward from the bottom of the thread guide 26 — maintaining the constant diameter $D_5$ — for a length $L_5$, where it ends.

In FIG. 3, the dental implant 10 of circular cross-section, is shown as having the threaded central cavity 28 of diameter $D_5$ — for the temporary securing of a healing screw which is subsequently replaced by a dental abutment — and the surface 24, tapering from a like diameter $D_5$ at it's junction with the central cavity 28, to the larger diameter $D_4$ at its junction with the included coronal lip 14. Such coronal lip 14, shown at the top of the dental implant 10, widens in a level plane from its interior diameter $D_4$, to its outer diameter $D_1$.

Figure 4:
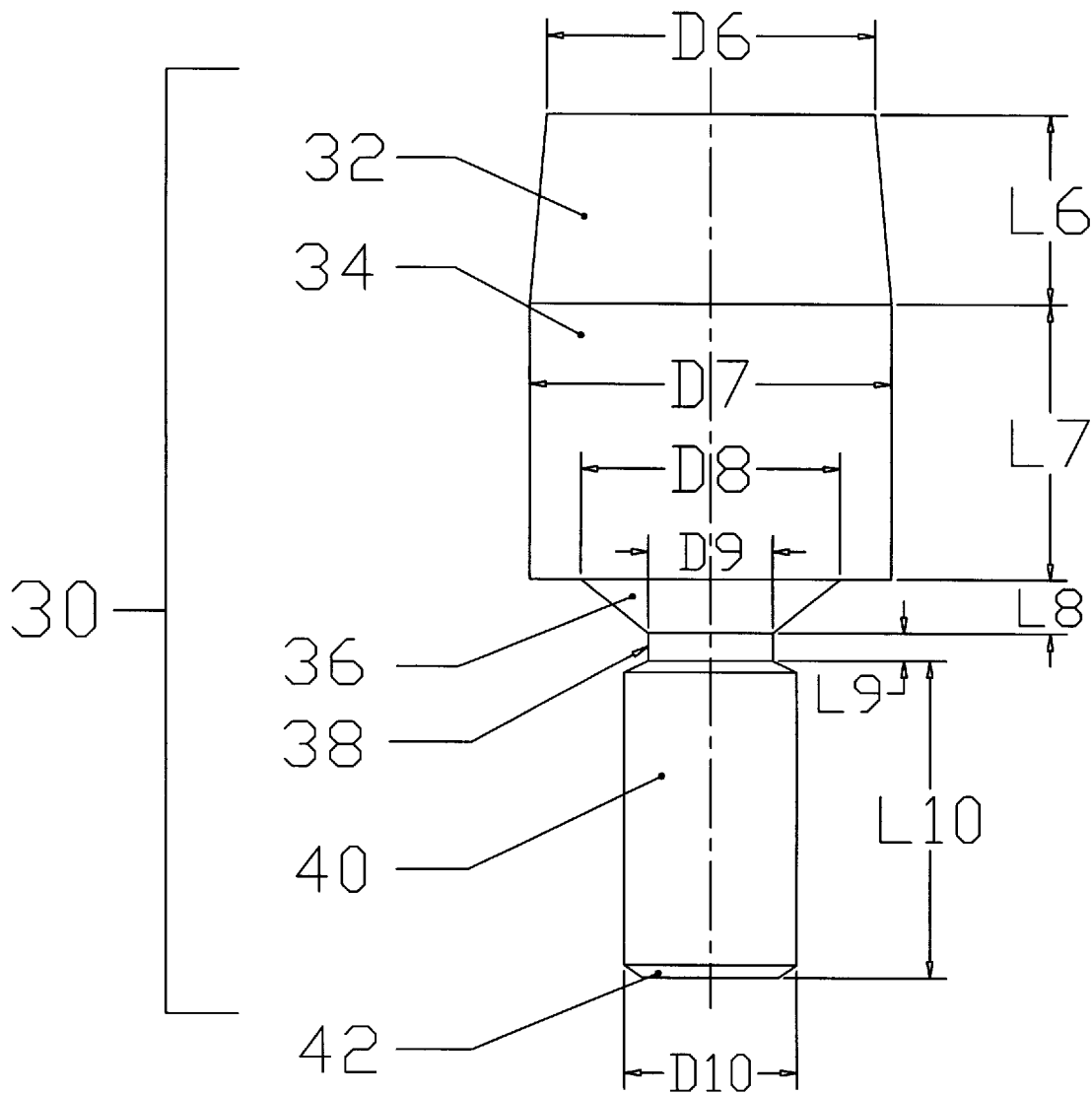
FIG. 4 is a side view of the dental abutment.

In FIG. 4, a dental abutment 30, — being round from its top perspective — is shown as having an upper body section 32, having a diameter $D_6$, which expands outward at approximately a 5-degree angle for a length $L_6$, where it becomes the lower body section 34. The lower body section 34, has a slightly larger diameter $D_7$ over its entire length $L_7$, where it becomes the segment junction 36. The segment junction 36, — which extends centrally from the lower body section 34 — tapers inwardly at a matching angle as 24 of FIG. 2, for a length $L_8$, — reaching a still smaller diameter $D_9$ — where it straightens out to form the thread undercut 38. The thread undercut 38, — which acts as an end to a threaded segment 40 — has a length $L_9$ before joining the threaded segment 40, — which has a tapered bottom 42 to permit easy insertion into the threaded central cavity 28 of FIG. 2 — and a diameter $D_{10}$, and of a length $L_{10}$.

Figure 5:
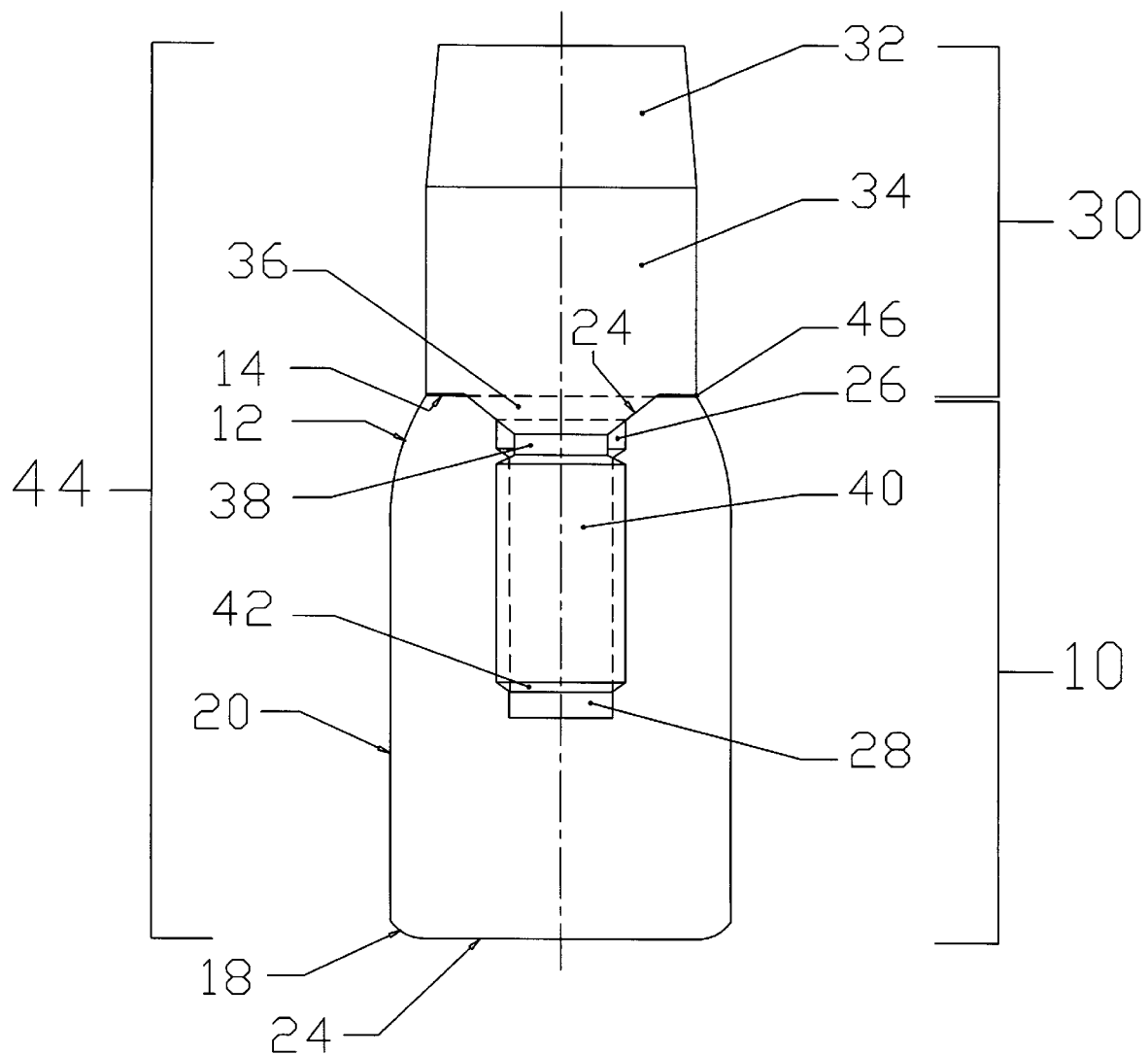
FIG. 5 is a side cut-away perspective view of the dental abutment showing its attachment to the implant in accordance with the teachings of the invention.

FIG. 5 shows the combination dental implant-abutment 44, — as it would be when the healing screw is replaced — showing the abutment 30, screwed into the dental implant 10 until the segment junction 36 abuts the surface 24 in a tight fit. Since the segment junction 36, has a length $L_8$ that is slightly greater than the depth of the surface 24, a shock absorbing gap 46 is formed between the bottom of the lower body section 34, and the coronal lip 14 — allowing the abutment to flex slightly as it is loaded by chewing forces.

In the operation of the invention, a dental professional exposes the bone in the edentulous area and drills a hole into which the dental implant 10 is to be inserted to a point at which the coronal lip 14 is flush with the crest of the bone. Since the bony socket created for the implant is of constant diameter and the implant has a radius surface 12, an annulus is created. This annulus is filled in with either freeze dried bone or bone filings which are created from the preparation of the implant socket. A barrier membrane is then laid over the crest of the bone and the implant 10 to prevent soft tissue from growing around the curved body section 12. A healing screw is then inserted through a hole in the barrier membrane and screwed into the threaded central cavity 28. The soft tissue is then closed over the healing screw and left for 3–8 months to allow the bone to integrate the implant. Surface 22 increases the stability and surface area of the implant.

After such time, the soft tissue is removed to expose the healing screw, which is then unscrewed and replaced with the abutment 30. The abutment 30, is screwed tightly into place causing the tapered surfaces 24 and 36 to meet, thereby creating a shock absorbing gap 46 between the implant 10 and the abutment 30. A false tooth is subsequently attached to the dental implant-abutment combination.

When the recipient of the dental implant-abutment combination chews, horizontal forces are exerted on the abutment 30. Some of the horizontal force that is produced is absorbed immediately by the flex allowed by the shock absorbing gap 46, with the remaining force being transferred to the implant 10. As will be understood, such force is transferred at two points between the abutment 30 and the implant 10. One such point — after flexure — is at the bottom outer edge of the abutment body 30, where the force is transferred vertically from the bottom of the lower body section 34 to the top the coronal lip 14, thereby relieving some of the horizontal force that stresses the crest of the bone. The other point is along the interface of surfaces 36, and 24, thereby shifting some of the horizontal force into the vertical plane, and further relieving the stress on the crest of the bone.

The horizontal force that remains, however, is exerted on the bearing surface below the crest of the bone, relieving the greatest concentration of stress, while lowering the axis of rotation. Thus, along with the curved body section 12 which gives the implant 10 its "barrel" shape, the construction effectively distributes the bending moment over a larger surface area of the implant.

The result of absorbing some of the shock of chewing, shifting horizontal forces into the vertical plane, lowering the axis of rotation, and increasing the surface area — increased moment of inertia that resists the bending moment, all are in a direction to reduce saucerization around the implant.

While there have been described what are considered to be preferred embodiments of the present invention, it will be readily appreciated by those skilled in the art that a single tooth replacement must have some means of preventing rotation, — such as a hex-nut — and that modifications can be made without departing from the scope of the teachings herein. Thus, whereas, a threaded body section has been depicted, it will be appreciated that other types of roughened surface may be employed on the outside of the implant. Additionally, while a vacant shock absorbing gap has been described, it will be understood that a shock absorbing material may be inserted between the abutment and the implant, and still carry out the principles underlying the invention. For at least such reasons, therefore, resort should be had to the claims appended hereto for a true understanding of the scope of the invention.

We claim:

1. A dental implant-abutment combination comprising an implant having a variable external diameter, a threaded central cavity, and a tapered opening of said cavity; an abutment body for the attachment of false teeth; with said abutment body having an upper body section, a lower body section, a segment junction centrally extending from said lower body section, and a threaded segment matching the internal threads of said central cavity for securely attaching to said implant; and wherein said segment junction is slightly longer than said tapered opening of said cavity to create a shock absorbing gap when said abutment is connected to said implant.

2. The dental implant-abutment combination of claim 1, wherein said implant has a curved body section to lower the implant's axis of rotation and increase the surface area — increase moment of inertia — resists the stresses of chewing.

3. The dental implant-abutment combination of claim 1, wherein said implant has a threaded outer surface to improve integration into bone during a healing process.

4. The dental implant-abutment combination of claim 1, wherein said tapered opening of said cavity is centrally located at a top section of said implant.

5. The dental implant-abutment combination of claim 4, wherein said opening tapers inwardly of said cavity at an angle to redirect forces applied in a horizontal plane, to a vertical plane.

6. The dental implant-abutment combination of claim 5, wherein said segment junction tapers inwardly at an angle from said lower abutment body section to form a flush fit with said tapered implant surface.

7. The dental implant-abutment combination of claim 4, wherein said segment junction tapers inwardly from said lower abutment body section to redirect forces applied to said abutment in a horizontal plane, to a vertical plane.

8. The dental implant-abutment combination of claim 1, wherein said shock absorbing gap is of dimension to permit the abutment to flex in response to the application of force applied to said abutment.

9. The dental implant-abutment combination of claim 1, wherein that portion of said implant which is closest to a connected abutment is of a smaller diameter than the diameter at any other portion of said implant.

10. The dental implant-abutment assembly of claim l, wherein said implant has a curved body section to lower the implant's axis of rotation and increase the surface area — increase moment of inertia — that resists the stresses of chewing.

11. The dental implant-abutment assembly of claim 9, wherein said opening tapers inwardly of said cavity at an angle to redirect forces applied in a horizontal plane, to a vertical plane.

12. The dental implant-abutment assembly of claim 9, wherein said implant has a threaded outer surface to improve integration into bone during a healing process.

13. The dental implant-abutment assembly of claim 12, wherein said abutment bears against said implant in the center thereof, on said threaded outer surface.

14. The dental implant-abutment assembly of claim 13, wherein said segment junction tapers inwardly at an angle from said lower abutment body section to form a flush fit with said tapered implant surface.

15. The dental implant-abutment assembly of claim 12, wherein said segment junction tapers inwardly from said lower abutment body section to redirect forces applied to said abutment in a horizontal plane, to a vertical plane.

16. The dental implant-abutment assembly of claim 12, wherein said segment junction is slightly longer than said tapered opening of said cavity to create a shock absorbing gap when said abutment is connected to said implant.

17. The dental implant-abutment combination of claim 16, wherein said shock absorbing gap is of dimension to permit the abutment to flex in response to the application of force applied to said abutment.

* * * * *